United States Patent [19]

Shippert

[11] Patent Number: 5,242,440
[45] Date of Patent: Sep. 7, 1993

[54] FINGER CONTROLLED SWITCHING APPARATUS

[76] Inventor: Ronald D. Shippert, 4975 S. Albion St., Littleton, Colo. 80121

[21] Appl. No.: 734,513

[22] Filed: Jul. 23, 1991

[51] Int. Cl.⁵ .................. A61N 3/00; H01H 35/00
[52] U.S. Cl. .................. 606/30; 200/DIG. 2; 606/40; 606/32; 606/49
[58] Field of Search .................. 606/27–32, 606/37, 38, 39, 40, 41, 42, 45, 49–52, 125; 128/897; 604/218, 187

[56] References Cited

U.S. PATENT DOCUMENTS

| | | | |
|---|---|---|---|
| 1,199,710 | 9/1916 | Newton | 200/DIG. 2 |
| 1,335,272 | 3/1920 | Broughton | 200/DIG. 2 |
| 1,527,792 | 2/1925 | French | 200/DIG. 2 |
| 1,906,193 | 4/1933 | Vitale | 200/DIG. 2 |
| 2,811,969 | 11/1957 | Shubert | 606/125 |
| 3,613,682 | 10/1971 | Naylor | 606/30 |
| 4,517,424 | 5/1985 | Kroczynski | 200/DIG. 2 |
| 4,722,625 | 2/1988 | O'Brien | 200/DIG. 2 |
| 5,045,650 | 9/1991 | Suzuki | 200/DIG. 2 |
| 5,097,252 | 3/1992 | Harvill et al. | 200/DIG. 2 |

Primary Examiner—Peter A. Aschenbrenner
Attorney, Agent, or Firm—Sheridan Ross & McIntosh

[57] ABSTRACT

A switching apparatus is provided includes an output device, a power supply for providing power to the output device and a finger-mounted switch connected between the output device and the power supply. When the finger to which the switch is mounted is in a first position, current flows from the power supply to the output device. When the finger is moved into a second position, current flow is prevented. In one embodiment, the output device is an electrosurgical cautery mounted on the finger in the same housing as the switch. The cautery tip extends from the housing and is energized when the finger is in the first position and is positioned within the housing and is deenergized when the finger is in the second position.

20 Claims, 4 Drawing Sheets

FINGER CONTROLLED SWITCHING APPARATUS

FIELD OF THE INVENTION

This invention relates to switching devices, and in particular, to a switch mounted on a finger and operated by changing the position of the finger.

BACKGROUND OF THE INVENTION

Small tools and instruments are extremely useful for performing work in small, crowded or otherwise hard to reach spaces. For example, during surgery a surgeon frequently uses a battery operated cautery to cauterize bleeding blood vessels. One such cautery resembles a penlight flashlight with a heating element extending from one end. When bleeding occurs during surgery, the surgeon lays down (or hands to a nurse) whatever instrument the surgeon has been using and asks a nurse for the cautery. The nurse picks up the cautery, removes a protective cap and hands the cautery to the surgeon. The surgeon takes the cautery and positions it in his or her hand such that the on-off switch (generally a momentary contact push switch) is properly located under the finger or thumb the surgeon uses to operate the switch. When cauterization is completed, the surgeon hands the cautery back to the nurse, picks up (or is handed) and positions another instrument in his or her hand and continues with the surgery. Simultaneously, the nurse replaces the protective cap over the cautery tip and places the unit on a stand, ready for its next use.

A significant drawback to such a device is that the exchange between nurse and surgeon may occur many times during surgery, a time consuming procedure which, because of the extra steps and personnel involved, can slow down or interrupt the flow of the surgery. Alternatively, if the surgeon lays the cautery down on the sterile surgical field without handing it back to the nurse, the hot tip may burn a hole in whatever it touches, such as paper draping material or a surgical glove, thus breaking the sterile field. And, the cylindrical shape of the cautery makes it prone to rolling and the instrument may roll onto the floor. An additional disadvantage is that the use of such a cautery is limited by the life of its non-replaceable, internal batteries. If the surgery is a long one or requires cauterization of many bleeding blood vessels, the batteries in the cautery may be exhausted before the surgery is completed, thus necessitating obtaining a replacement unit.

Other medical devices, such as flashlights and suction apparatus, have some of the same drawbacks as the portable cautery just described. That is, they may require time consuming handling by various personnel and may require additional manipulation by the surgeon before they can be used. Furthermore, the limited battery life of some instruments can limit their usefulness, especially during long procedures. Similarly, small tools and instruments used by non-medical personnel also have some of the same drawbacks. For example, small flashlights, soldering guns, blowers and vacuums are used by jewelers, electricians, mechanics and model builders and require similar handling and manipulation as the small medical devices.

It is known to use switches to control electrical devices, such as medical instruments. Some electrosurgical instruments, such as those disclosed in U.S. Pat. Nos. 4,552,143 by Lottick and 4,041,952 by Morrison, Jr. et al., employ switches which are mounted on the side of the instrument. To operate such an instrument, the surgeon holding the instrument presses and releases a button to activate and deactivate the instrument.

Other instruments employ switches located remote from the instrument. U.S. Pat. No. 702,472 by Pignolet discloses surgical forceps connected to a source of electric energy. The tissue to be cauterized is grasped and the unit is activated by a remote switch allowing current to flow to a heating element in one or both of the forcep jaws. When cauterization is complete, the tissue is released and the switch turned off. U.S. Pat. No. 3,845,771 by Vise discloses an electrosurgical glove which has an electrical contact pad on the outside surface of at least one of the digits of the glove. A lead embedded in the glove is connected to a current or radio frequency energy source. To use, the wearer of the glove picks up an electrically conductive instrument making sure that the contact pad on the glove makes proper contact with the instrument. The user turns on a separate switch to provide current or radio frequency energy from the source through the glove to the instrument.

Still other electrosurgical devices have integrated switches in which a mechanical operation simultaneously activates or deactivates an electrical circuit. U.S. Pat. No. 2,012,937 by Beuoy discloses Y-shaped electrical caponizing forceps having a cauterizing bar extending across the forked end of the forceps. The forceps are connected to an electrical power source and, when the two arms of the forceps are squeezed together, electrical contact is made sending current to the cauterizing bar. When the forceps are released, the cauterizing bar turns off.

Consequently, it is desirable for small instruments and tools to be easy to activate and deactivate and be readily available without necessitating extra steps by the user or support personnel. It is further desirable that medical instruments be quickly available but without risk to the sterile surgical field, that they be light weight and that their battery life be extendable.

SUMMARY OF THE INVENTION

In accordance with the present invention, a finger-controlled electrical switching apparatus is provided that includes an electrical device to which the flow of current is controlled. When the finger is in a first position, current is supplied to the device. When the finger is in a second position, there is no current flow to the device. In one embodiment, the apparatus includes an electrosurgical instrument, such as a cautery.

The switching apparatus includes an interconnect mechanism, one end of which is removably secured to one portion of a human finger. The interconnect mechanism has two electrical terminals secured to a holder, one terminal connected to a first terminal of a power supply and the second connected to a first terminal of an instrument. A second terminal of the instrument is connected to a second terminal of the power supply.

The finger-mounted switching apparatus also includes a housing mounted on the fingertip and an electrically conductive plate. The holder having the terminals is positioned inside the housing and is slidable relative thereto while the other end of the interconnect mechanism is fastened to the finger closer to the hand, preferably to the metacarpus. When the finger is moved into a first position, preferably into a straightened position, the distance between the fingertip and the portion of the finger on which the interconnect mechanism is fastened decreases, causing the housing to slide or move relative to the holder until both terminals of the interconnect mechanism are in electrical contact with the conductive plate completing the circuit between the power supply and the instrument. When the finger is moved into a second position, preferably into a bent position, the distance between the fingertip and the portion of the finger on which the interconnect mechanism is fastened increases, causing the housing to slide in the opposite direction until the terminals are no longer in electrical contact with the conductive plate and breaking the circuit.

In one aspect of the present invention, the conductive plate is fixed to the inside of the housing in opposing relation to the terminals. When the finger is moved into the first position, the housing and conductive plate slide in one direction relative to the holder and terminals until electrical contact is made between the two terminals and the conductive plate. When the finger is moved into the second position, the housing and conductive plate slide in the opposite direction relative to the holder and the terminals until electrical contact is broken. In another aspect, the conductive plate is fixed to the holder and is biased such that when the finger is moved into the first position, the conductive plate is urged against both terminals by the inside of the housing, completing the circuit. When the finger is moved into the second position, the conductive plate springs away from at least one terminal, breaking the circuit.

The instrument, such as a cautery probe, can be secured to an end of the holder. Consequently, when the finger is moved into the first (preferably straightened) position, the probe extends out of the housing and is activated by the electrical circuit completed by the conductive plate. When the finger is moved into the second (preferably bent) position, the cautery probe is positioned within the housing and is deactivated. Thus, the cautery is always available to the surgeon and can be quickly used without the need for additional personnel. When not in use, the cautery remains on the surgeon's finger with the tip retracted so that the risk of contamination of the sterile surgical field is substantially reduced.

In one embodiment, the power supply is a battery pack which can be assembled prior to surgery with an appropriate number of batteries corresponding to the anticipated length of surgery. In the event that additional battery capacity is needed during surgery, additional batteries can be added or a new battery pack can be snapped into place. The battery pack can be strapped onto the surgeon's wrist or arm.

Although the present invention has been described in connection with a medical instrument (in particular, a cautery), it can also be used with other small tools and instruments. For example, the present invention can be adapted to a small soldering gun for use by an electrical technician. The present invention is also adaptable to provide a finger-mounted suction tip activated by finger position. Such a device would be useful for jewelers, hobbyists or other people needing to manipulate and assemble very small parts. Similarly, the present invention can be adapted to provide a finger-mounted, finger operated flashlight or small blower.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
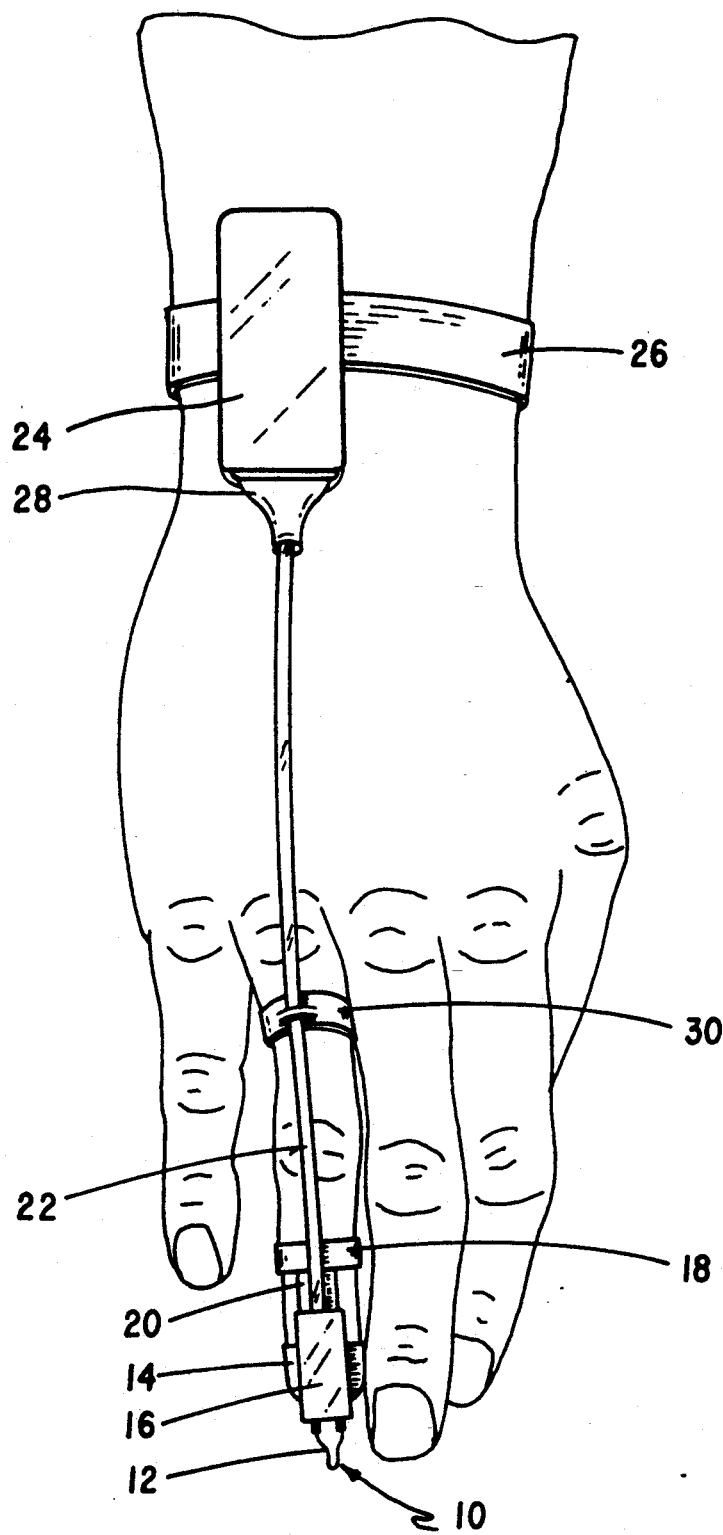
FIG. 1 illustrates a preferred embodiment of the present invention in which the finger-controlled switching apparatus includes an electrosurgical cautery.

FIG. 1 illustrates an embodiment of the present invention in which a finger-controlled switching apparatus 10 includes an electrosurgical cautery, shown here with its tip 12 in an extended position. For convenience, switching apparatus 10 is mounted on the third finger of the surgeon's hand. Thus mounted, it will not interfere with the surgeon's use of the first two fingers of the hand when, for example, the surgeon uses a scalpel or forceps. It can be appreciated, however, that switching apparatus 10 can be mounted on any of the fingers, or even the thumb.

Switching apparatus 10 includes a finger-cup 14 into which the tip of the surgeon's finger is inserted. A housing 16 is secured to finger-cup 14 to enclose certain elements of switching apparatus 10 as well as cautery tip 12 when it is retracted. Finger-cup 14 and housing 16 can be formed of a lightweight, flexible plastic. They are preferably secured in place on the finger with a first adjustable ring 18. Preferably, first adjustable ring 18 is made of a thin strip of metal, such as aluminum, which is flexible enough to be bent around the finger but is stiff enough to retain its bent shape until removed. The metal ring can be covered by a layer of plastic material of the same type which is used to form finger-cup 14 and housing 16. A strip 20 of the same material connects first adjustable ring 18 with finger-cup 14 and housing 16.

Switching apparatus 10 also includes an interconnect mechanism 22 which electrically connects electrosurgical cautery 12 with a power supply 24. In the embodiment shown in FIG. 1, power supply 24 is a disposable battery pack, containing one or more batteries to provide power to cautery tip 12 and is secured to the surgeon's arm with a strap 26. The number of batteries, and their type, in the battery pack can be determined prior to surgery. For example, two 1½ volt batteries connected in series may be adequate. Longer power life may be achieved by using a battery pack that includes more than one set of batteries. Other combinations are, of course, possible. In the event that there is insufficient power, the battery pack can be disconnected from a battery clip 28 on one end of interconnect mechanism 22 and replaced with a new battery pack. Depending on the instrument that is part of the switching apparatus 10, other types of power supplies, both AC and DC, can be connected to interconnect mechanism 22.

Interconnect mechanism 22 preferably includes insulated wires which are embedded in a sheath that should be sufficiently rigid to permit relative sliding motion of certain elements of switching apparatus 10, as will be detailed below, but should also be flexible enough to permit the surgeon's finger to bend and operate the switching apparatus 10. A second adjustable ring 30 secures interconnect mechanism 22 to the surgeon's finger. Second adjustable ring 30, like first adjustable ring 18, is preferably made of a flexible strip of metal, such as aluminum, encased in a flexible plastic. The second ring 30 enables the apparatus to be adjusted for use with and connected to different length fingers.

Figure 2:
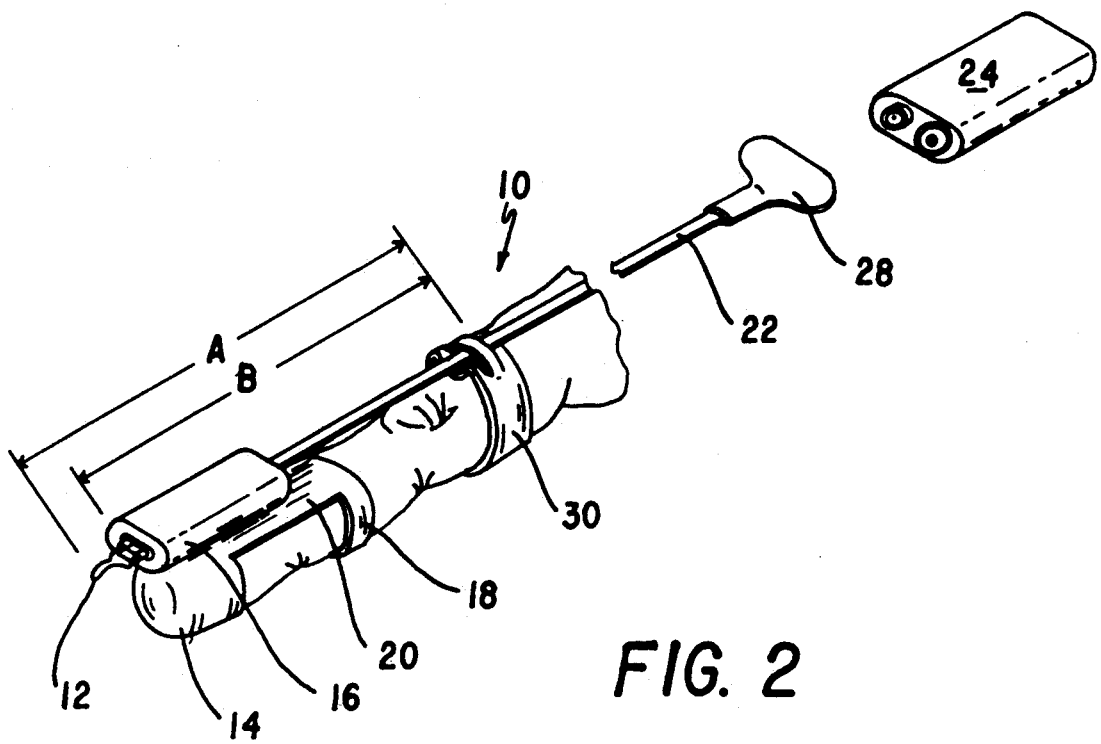
FIG. 2 illustrates the finger-controlled switching apparatus of FIG. 1 mounted on a human finger with the cautery tip extended relative to the housing.
Figure 3:
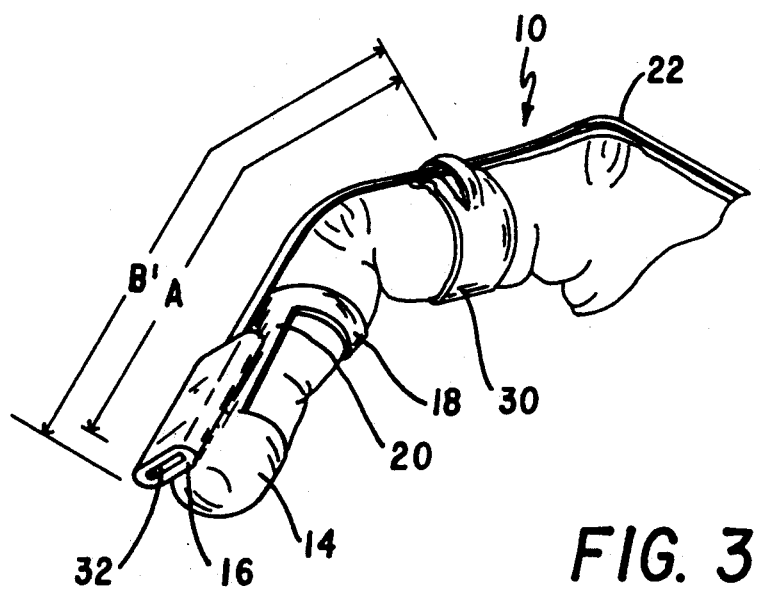
FIG. 3 illustrates the finger-controlled switching apparatus of FIG. 1 mounted on a human finger with the cautery tip retracted relative to the housing.

FIGS. 2 and 3 illustrate the finger-controlled switching apparatus 10 and cautery 12 in their activated and deactivated positions. FIG. 2, like FIG. 1, shows cautery tip 12 in its extended position while in FIG. 3, cautery tip 12 is in its retracted position. In operation, when the surgeon's finger is moved into a substantially straight position, as shown in FIG. 2, cautery tip 12 extends and switching apparatus 10 permits current to flow from power supply 24 through interconnect mechanism 22 and into cautery tip 12, heating it up for use. When the surgeon's finger is bent, as shown in FIG. 3, cautery tip 12 retracts into housing 16 and switching apparatus 10 prevents current from flowing from power supply 24 to cautery tip 12, turning it off.

Cautery tip 12 is secured to a holder at the end of interconnect mechanism 22 opposite battery clip 28. Because interconnect mechanism 22 is clamped to the finger with second adjustable ring 30, the distance A between cautery tip 12 and second adjustable ring 30 is fixed and does not change when the finger is bent, as illustrated in FIG. 3. On the other hand, the distance between second adjustable ring 30 and the end of finger-cup 14 does depend upon the position of the surgeon's finger. When the finger is substantially straight, the distance between second adjustable ring 30 and the end of finger-cup 14 is a first distance B' as measured along the top of the finger. When the finger is bent, the slides along interconnect mechanism 22, away from second adjustable ring 30, to cover cautery tip 12. Put another way, cautery tip 12 retracts into housing 16. It can be appreciated, therefore, that interconnect mechanism 22 must be rigid enough to permit housing 16 to slide easily over it but it should not be so rigid that it inhibits or prevents the finger from moving between the straightened and bent positions illustrated in FIGS. 2 and 3.

Figure 5:
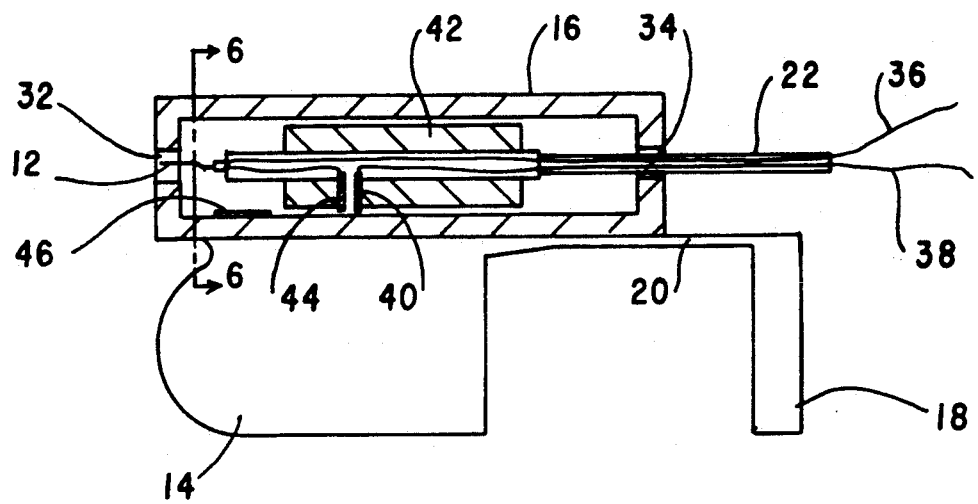
FIG. 5 illustrates a cross-sectional view of the embodiment illustrated in FIG. 3 with the cautery tip retracted and deactivated.
Figure 4:
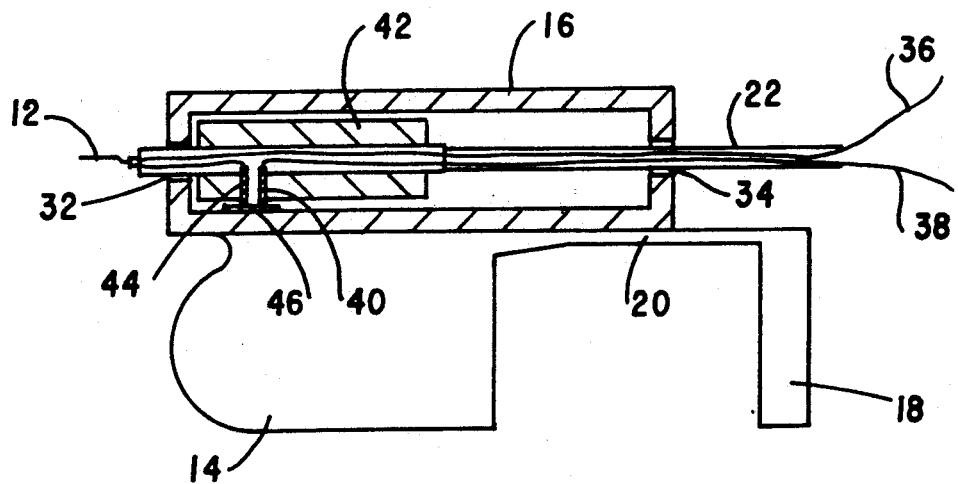
FIG. 4 illustrates a cross-sectional view of the embodiment illustrated in FIG. 2 with the cautery tip extended and activated.

FIGS. 4 and 5 are cross-sectional views of switching apparatus 10 with cautery tip 12 in the extended and retracted positions, respectively. Housing 16 includes a front opening 32, through which cautery 12 extends and retracts, and a rear opening 34, through which portions of interconnect mechanism 22 enter. Interconnect mechanism 22 includes a first wire 36 and a second wire 38. First wire 36 is coupled between a first terminal of battery clip 28 and a first terminal of cautery tip 12. Second wire 38 is coupled between a second terminal of battery clip 28 and a first contact pin 40 protruding through one surface of a holder 42 within housing 16. A second terminal of cautery tip 12 is coupled to a second contact pin 44 which also protrudes through the surface of holder 42. A conductive plate 46 is secured to the inside of housing 16. Conductive plate 46 can be secured to the surface of housing 16 or it can be secured in a recess so that its surface is flush with the inside surface of housing 16.

Conductive plate 46 is at least as long as the distance between first and second contact pins 40 and 44 so that, with the finger in a substantially straightened position and cautery tip 12 extending through front opening 32, first and second contact pins 40 and 44 both make electrical contract with conductive plate 46. An electrical circuit is thereby completed between power supply 24 and cautery tip 12. When the finger is moved into its bent position, housing 16 and conductive plate 46 move or slide relative to interconnect mechanism 22 including the contact pins 40 and 44. After sufficient sliding movement, conductive plate 46 is no longer in electrical contact with first and second contact pins 40 and 44, thus breaking the circuit between power supply 24 and cautery tip 12.

Figure 6:
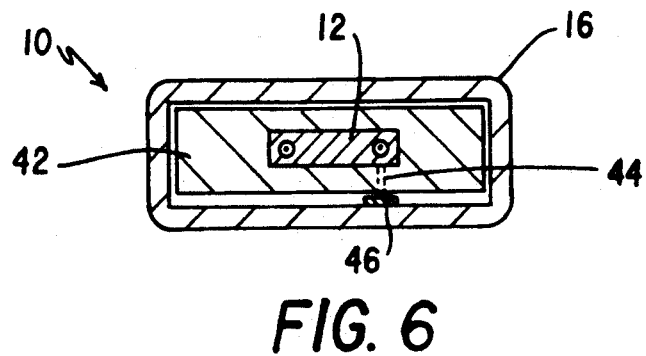
FIG. 6 illustrates a cross-sectional view of the embodiment illustrated in FIG. 5 taken along the line 6—6.

FIG. 6 is a cross-sectional view of switching apparatus 10 taken across line 6—6 of FIG. 5. It can be appreciated that holder 42 of interconnect mechanism 22 should slide smoothly within housing 16. One factor which contributes to the ease with which holder 42 slides within housing 16 is the distance between holder 42 and housing 16 on all four sides. The distances should be great enough to permit holder 42 to slide within housing 16 but should be small enough to prevent holder 42 from wiggling or twisting within housing 16. Such motion could prevent one or both of first and second contact pins 40 and 44 from making good electrical contact with conductive plate 46. Such motion can also limit the accuracy with which cautery tip 12 is used by the surgeon. A second factor affecting the ease with which holder 42 slides within housing 16 is the materials with which they are made. If the coefficient of friction between the two is great enough, then holder 42 will not slide smoothly within housing 16. Instead, interconnect mechanism 22 will likely bend improperly when the finger is moved from a bent position to a substantially straightened position, thereby preventing or inhibiting movement of holder 42 within housing 16. If desired, the relative coefficient of friction can be reduced by disposing friction reducing material on one or more of the inside surfaces of housing 16 or on one or more of the outside surfaces of holder 42. For example, a Teflon film can be used to improve the desired sliding action. And, a third factor is the stiffness of interconnect mechanism 22. As previously discussed, interconnect mechanism 22 must be sufficiently rigid to permit the sliding of housing 16 relative to interconnect mechanism 22 but should not be so rigid that movement of the surgeon's finger is inhibited or prevented.

Figure 8:
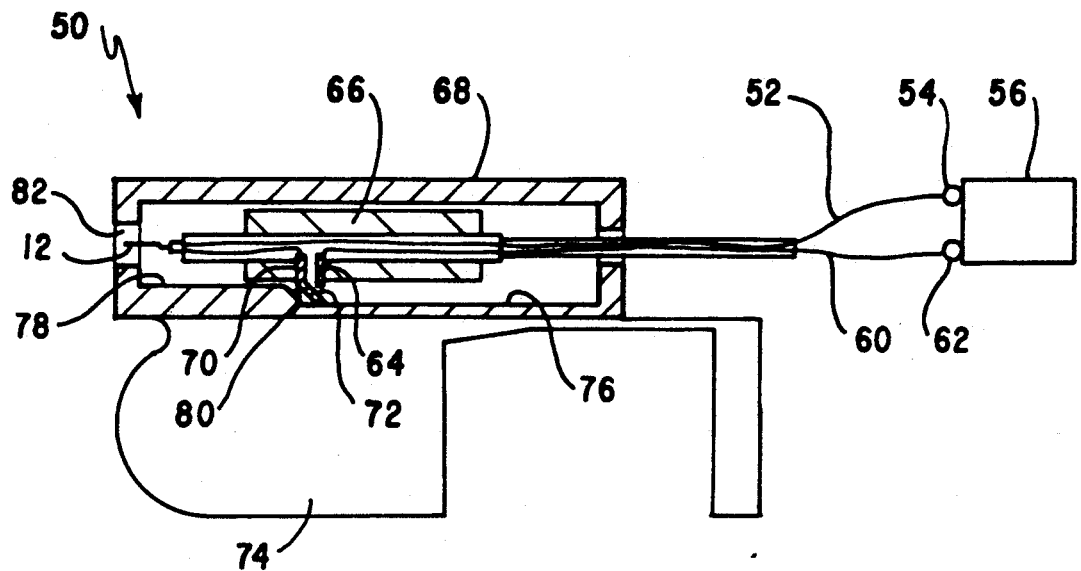
FIG. 8 illustrates a cross-sectional view of the embodiment illustrated in FIG. 7 with the cautery tip retracted and deactivated.
Figure 7:
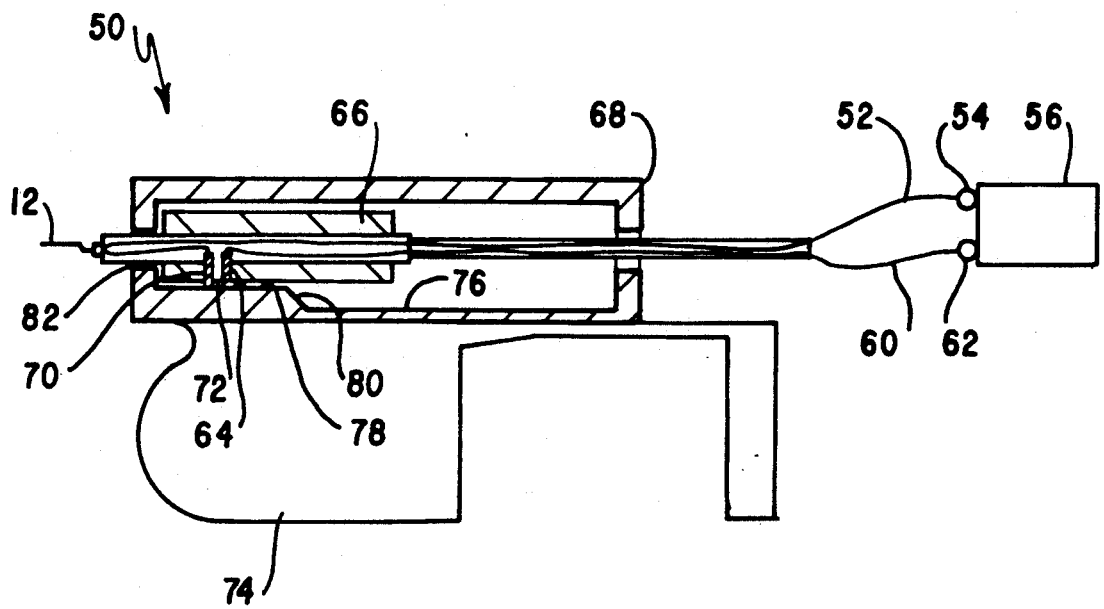
FIG. 7 illustrates a cross-sectional view of another embodiment of the present invention with the cautery tip extended and activated.

FIGS. 7 and 8 illustrate another embodiment of a switching apparatus 50 of the present invention. A first wire 52 is coupled between a first terminal 54 of battery 56 and a first terminal of an electrosurgical device, such as cautery tip 58. A second wire 60 is coupled between a second terminal 62 of battery 56 and a first contact pin 64 protruding through one surface of a holder 66 within a housing 68. A second terminal of cautery tip 58 is coupled to a second contact pin 70 which also protrudes through the surface of holder 66. A conductive plate 72 is physically and electrically secured to second contact pin 70 and extends to, or just beyond, first contact pin 64. Conductive plate 72 is biased such that, in the absence of pressure against it, it does not contact first contact pin 64. For example, conductive plate 72 can be soldered to second contact pin 70. The solder joint provides sufficient resiliency to permit the necessary movement of conductive plate 72 without inhibiting move of holder 66 relative to housing 68. Secured to the outside of housing 68 is a finger-cup 74 into which the tip of the surgeon's finger is inserted.

The inside surface of housing 68 facing the portion of holder 66 on which first and second contact pins 64 and 70 and conductive plate 72 are disposed is formed in such a way as to have a lower surface 76, an upper surface 78 and a sloped surface 80 therebetween. When cautery tip 56 is positioned within housing 68, as illustrated in FIG. 8, first and second contact pins 64 and 70 and conductive plate 72 are positioned opposite a portion of lower surface 76 such that conductive plate 72 does not contact first contact pin 64, thereby deactivating cautery tip 56. When the finger on which switching device 50 is secured is straightened, cautery tip 56 extends through an opening 82 in the front of housing 68, as illustrated in FIG. 7, and housing 68 slides relative to holder 66. Sloped surface 80 urges conductive plate 72 against first contact pin 64 and is maintained in that position by upper surface 78. Consequently, the electrical circuit is completed and cautery tip 56 is activated.

Although the present invention has been described in detail, it should be understood that various changes, substitutions and alterations can be made herein within without departing from the spirit and scope of the invention as defined by the appended claims. For example, although switching apparatus 10, as described herein with respect to FIGS. 4–6, incorporates a single-pole, single-throw switch, an alternative embodiment can employ a single-pole, double-throw mechanism. In this embodiment, a third contact pin protrudes from holder 42. Conductive plate 46 alternately connects one of two circuits as the finger moves between the bent and substantially straightened positions. In another embodiment, a multiple-pole, single- or double-throw mechanism could be used. In this embodiment, additional, parallel sets of contact pins and conductive plates could be employed to provide a broader range of control of various circuits.

In other embodiments, other small instruments or tools, both surgical and non-surgical, could be secured to holder 42 or the like and electrically controlled.

What is claimed is:

1. An electrosurgical apparatus, comprising:
   first means for providing heat, said first means including a cautery;
   second means for supplying current to said cautery;
   third means for controlling current between said cautery and said second means, said third means including electrical switch means having first and second terminals and electrical contact means for switchably electrically interconnecting said first and second terminals, at least one of said first terminal, said second terminal and said electrical contact means slides between first and second positions of said electrical switch means, said first position for use in providing electrical current to said cautery and said second position for use in removing electrical current from said cautery, wherein during said sliding, said at least one of said first terminal, said second terminal and said electrical contact means moves and in which said cautery also moves during said sliding, said third means further including housing means for containing said electrical switch means and mounting means for holding said housing means to a human finger; and
   fourth means for providing electrical communication between said electrical switch means and said second means, wherein said second means is electrically connected to said electrical switch means using said fourth means and said cautery is electrically connected to said electrical switch means.

2. An apparatus of claim 1 wherein said cautery has a tip to which current is applied when said electrical switch means is in said first position and current being removed from said tip when said electrical switch means is in said second position.

3. An apparatus of claim 1 wherein said second means includes battery power means with said battery power means being connected to said electrical switch means using said fourth means.

4. An apparatus of claim 3 wherein said battery power means is detachably coupled to said fourth means.

5. An apparatus of claim 1 wherein said electrical contact means comprises an electrically conductive plate, said plate being movable relative to said first and second electrical terminals when said switch means moves between said first and second positions thereof.

6. An apparatus of claim 5 wherein:
   said third means includes housing means for enclosing said first and second terminals.

7. An apparatus of claim 6 wherein said third means includes cup means joined to said housing means and a first ring portion.

8. An apparatus of claim 6 wherein said fourth means includes a second ring portion, said fourth means being sufficiently rigid to permit said conductive plate to move relative to said housing means.

9. An apparatus of claim 1, wherein said fourth means includes:
   a wire for electrically coupling said second means and said third means; and
   a sheath surrounding said wire that is sufficiently rigid to permit relative movement between said electrical switch means and said housing means.

10. An apparatus of claim 5 wherein: said plate being in electrical contact with said first terminal and biased away from said second terminal.

11. An apparatus of claim 10 wherein:
   said third means includes housing means for enclosing said first and second terminals, said housing means having a sloped inner surface for urging said plate against said second terminal.

12. A method for controlling current to an electrosurgical apparatus, comprising the steps of:
   securing a switch to a human finger, said switch being movable between a first state and a second state and said switch being contained in housing means;
   positioning the human finger in a first position thereby causing said switch to be in said first state and a cautery to be positioned outwardly of said housing means whereby said switch allows current to flow from a power source to said cautery; and
   positioning the human finger in a second position thereby causing said switch to be in said second state and substantially all of said cautery being contained in said housing means whereby said switch prevents current from flowing from said power source to said cautery.

13. A method of claim 12 wherein said step of positioning the human finger in said second position said switch to be in said second state includes the step of:
locating substantially all of said cautery within said housing means.

14. A method of claim 12 wherein said step of positioning the finger in the first position said switch in said first state includes the step of:
causing a conductive plate secured to a first portion of the finger to move relative to first and second contact pins until said first and second contact pins are in electrical contact with said conductive plate.

15. A method of claim 12 wherein said step of positioning the finger in the second position said switch in said second state includes the step of:
causing a conductive plate secured to a first portion of the finger to move relative to first and second contact pins until said first and second contact pins are electrically separated from said conductive plate.

16. A method of claim 12 wherein said step of positioning the finger in the first position said switch in said first state includes the step of:
causing a conductive plate in electrical contact with a first contact pin and biased away from a second contact pin to be urged against said second contact pin until said conductive plate is in electrical contact with said second contact pin.

17. A method of claim 12 wherein said step of positioning the finger in the second position said switch in said second state includes the step of:
causing a conductive plate in electrical contact with a first contact pin and biased away from a second contact pin to move away from said second contact pin until said conductive plate is electrically separated from said second contact pin.

18. An electrosurgical apparatus, comprising:
a power source;
a cautery for switchably receiving electrical current from said power source;
switch means disposed between said power source and said cautery, said switch means able to be mounted to a human finger and having first and second switch positions, each of said switch positions depending upon a position of the human finger to which said switch means is attached; and
housing means having an opening for removably receiving said cautery, substantially all of said cautery being located outwardly of said housing means when said switch means is in said first position when current is provided from said power source to said cautery through said switch means and substantially all of said cautery being contained in said housing means when electrical current is not provided to said cautery.

19. An apparatus of claim 18, wherein:
said housing means contains substantially all of said switch means.

20. An apparatus of claim 19, wherein:
said switch means includes first and second terminals and electrical contact means for electrically interconnecting said first and second terminals and in which at least one of said first terminal, said second terminal and said electrical contact means slides when said switch means changes between said first and second positions and, during said sliding, said cautery moves relative to said housing means.

* * * * *